(12) United States Patent
Miller et al.

(10) Patent No.: US 8,884,247 B2
(45) Date of Patent: Nov. 11, 2014

(54) SYSTEM AND METHOD FOR EX SITU ANALYSIS OF A SUBSTRATE

(71) Applicant: FEI Company, Hillsboro, OR (US)

(72) Inventors: Thomas G. Miller, Portland, OR (US);
Jason Arjavac, Hillsboro, OR (US);
Damon Heer, Beaverton, OR (US);
Michael Strauss, Hillsboro, OR (US);
Gerardus Nicolaas Anne van Veen,
Waalre (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/626,193

(22) Filed: Sep. 25, 2012

(65) Prior Publication Data

US 2014/0084157 A1 Mar. 27, 2014

(51) Int. Cl.
*G01N 1/28* (2006.01)
*H01J 37/02* (2006.01)
*H01J 37/305* (2006.01)
*H01J 37/20* (2006.01)
*G01N 1/32* (2006.01)

(52) U.S. Cl.
CPC .............. *G01N 1/28* (2013.01); *H01J 37/3056* (2013.01); *H01J 37/02* (2013.01); *H01J 37/20* (2013.01); *G01N 1/32* (2013.01)
USPC ...... 250/442.11; 250/307; 250/310; 250/311; 250/440.11; 250/492.3

(58) Field of Classification Search
USPC .................... 250/306, 307, 310, 311, 440.11, 250/442.11, 491.1, 492.1, 492.2, 492.21, 250/492.3
See application file for complete search history.

(56) References Cited

U.S. PATENT DOCUMENTS

| | | | | |
|---|---|---|---|---|
| 6,002,136 | A * | 12/1999 | Naeem ...................... | 250/442.11 |
| 6,674,078 | B2 * | 1/2004 | Nagayama et al. ........... | 250/311 |
| 6,717,156 | B2 * | 4/2004 | Sugaya et al. ........... | 250/440.11 |
| 7,196,338 | B2 * | 3/2007 | Holloway ................ | 250/440.11 |
| 7,348,570 | B2 * | 3/2008 | Allred et al. ............. | 250/440.11 |
| 7,611,610 | B2 | 11/2009 | Nadeau et al. | |
| 7,678,337 | B2 | 3/2010 | Sage et al. | |
| 8,099,792 | B1 * | 1/2012 | Hersam et al. .................. | 850/19 |
| 8,163,145 | B2 | 4/2012 | Nadeau et al. | |
| 8,253,118 | B2 | 8/2012 | Zhang et al. | |
| 8,314,409 | B2 | 11/2012 | Miller et al. | |

(Continued)

FOREIGN PATENT DOCUMENTS

WO 2013082496 6/2013

OTHER PUBLICATIONS

Giannuzzi et al. "FIB Lift-Out for Defect Analysis" Microelectronic Failure Analysis Desk Reference 2002 Supplement.*

(Continued)

*Primary Examiner* — Michael Logie
(74) *Attorney, Agent, or Firm* — Scheinberg & Associates, PC; Michael O. Scheinberg; Ki O

(57) ABSTRACT

A method and system for creating an asymmetrical lamella for use in an ex situ TEM, SEM, or STEM procedure is disclosed. The shape of the lamella provides for easy orientation such that a region of interest in the lamella can be placed over a hole in a carbon film providing minimal optical and spectral interference from the carbon film during TEM, SEM, or STEM procedure of chemical analysis.

7 Claims, 10 Drawing Sheets

(56) References Cited

U.S. PATENT DOCUMENTS

| | | |
|---|---|---|
| 8,357,913 B2 | 1/2013 | Agorio et al. |
| 8,581,205 B2 * | 11/2013 | Wei et al. .................. 250/440.11 |
| 2002/0166976 A1 * | 11/2002 | Sugaya et al. ........... 250/440.11 |
| 2008/0296498 A1 * | 12/2008 | Hong .......................... 250/311 |
| 2010/0305747 A1 * | 12/2010 | Agorio et al. ................. 700/213 |
| 2010/0308219 A1 * | 12/2010 | Blackwood et al. .......... 250/307 |
| 2011/0006207 A1 * | 1/2011 | Arjavac et al. ................ 250/307 |
| 2011/0027486 A1 * | 2/2011 | Jiang et al. .................... 427/331 |
| 2011/0115129 A1 | 5/2011 | Straw et al. |
| 2011/0163068 A1 | 7/2011 | Utlaut et al. |
| 2011/0192988 A1 * | 8/2011 | Feng et al. ............... 250/440.11 |
| 2011/0204225 A1 * | 8/2011 | Shichi et al. .................. 250/310 |
| 2012/0091360 A1 | 4/2012 | Zhang et al. |
| 2012/0103945 A1 | 5/2012 | Straw et al. |
| 2012/0199923 A1 | 8/2012 | Nadeau et al. |
| 2012/0217152 A1 | 8/2012 | Miller |
| 2013/0092826 A1 | 4/2013 | Miller et al. |
| 2013/0214468 A1 * | 8/2013 | Giannuzzi .................... 269/287 |
| 2013/0341505 A1 * | 12/2013 | Arjavac et al. ................ 250/307 |

OTHER PUBLICATIONS

Quantifoil, "Support Films for Electron Microscopy", Quantifoil Micro Tools GmbH (2003).*

'Tilted Attachment of Lamella to Notched Sample Grid,' http://ip.com/IPCOM/000178062, Jan. 14, 2009, 2 pgs.

* cited by examiner

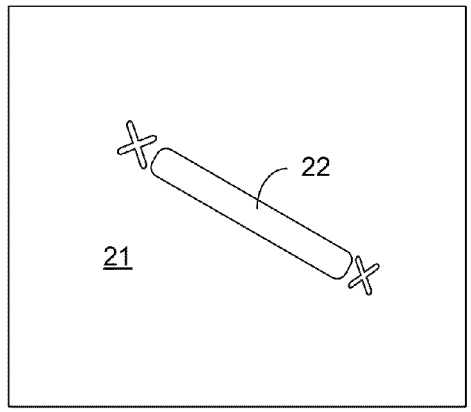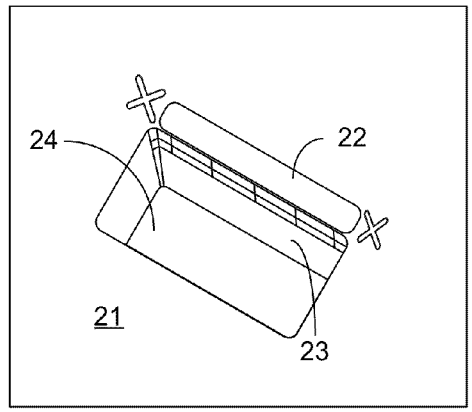
FIG. 2
Prior Art
FIG. 3
Prior Art
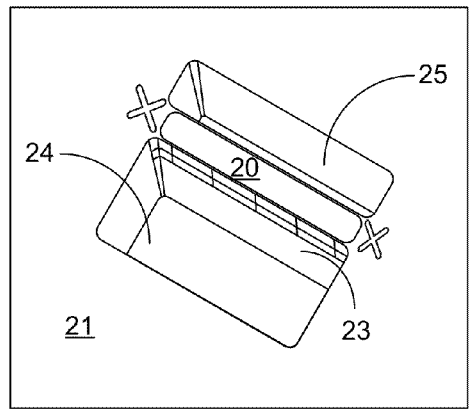
FIG. 4
Prior Art

REPLACEMENT DRAWINGS
4 / 10
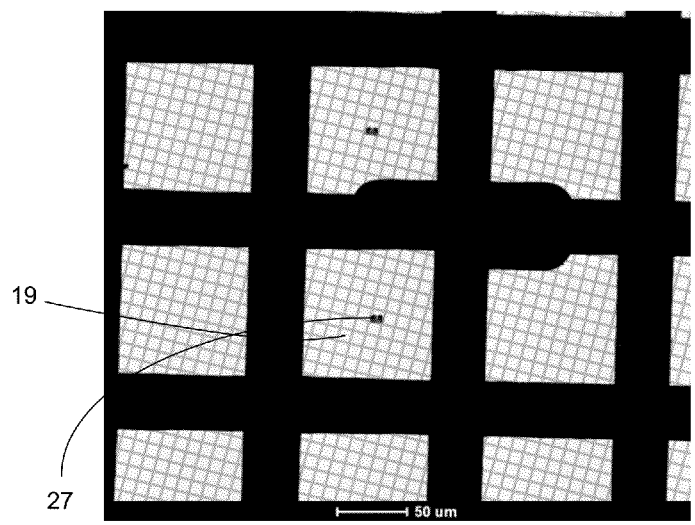
FIG. 8
Prior Art
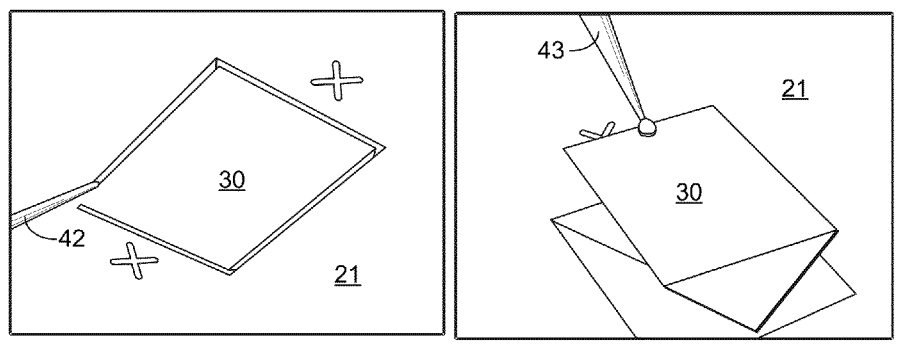
FIG. 9
Prior Art
FIG. 10
Prior Art Rotate

SYSTEM AND METHOD FOR EX SITU ANALYSIS OF A SUBSTRATE

TECHNICAL FIELD OF THE INVENTION

The present invention relates to preparation of samples and methods of sample handling for analysis by electron microscopes.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting metallization lines, spacing and diameter of contact holes and vias, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and to assure a desired device geometry.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast to SEMs, which only image the surface of a material, TEMs allows the additional capability to analyze the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Samples are typically less than 100 nm thick.

In a scanning transmission electron microscope (STEM), a primary electron beam is focused to a fine spot, and the spot is scanned across the sample surface. Electrons that are transmitted through the substrate are collected by an electron detector on the far side of the sample, and the intensity of each point on the image corresponds to the number of electrons collected as the primary beam impacts a corresponding point on the surface.

As semiconductor geometries continue to shrink, manufacturers increasingly rely on transmission electron microscopes (TEMs) for monitoring the process, analyzing defects, and investigating interface layer morphology. The term "TEM" as used herein refers to a TEM or a STEM, and references to preparing a sample for a TEM are to be understood to also include preparing a sample for viewing on an STEM. Because a sample must be very thin for viewing with transmission electron microscopy (whether TEM or STEM), preparation of the sample can be delicate, time-consuming work.

Thin TEM samples cut from a bulk sample material are known as "lamellae". Lamellae are typically less than 100 nm thick, but for some applications a lamella must be considerably thinner. With advanced semiconductor fabrication processes at 30 nm and below, a lamella needs to be less than 20 nm in thickness in order to avoid overlap among small scale structures. Currently, thinning below 30 nm is difficult and not robust. Thickness variations in the sample result in lamella bending, overmilling, or other catastrophic defects. For such thin samples, lamella preparation is a critical step in TEM analysis that significantly determines the quality of structural characterization and analysis of the smallest and most critical structures.

Several techniques are known for preparing TEM specimens. These techniques may involve cleaving, chemical polishing, mechanical polishing, or broad beam low energy ion milling, or combining one or more of the above. The disadvantage to these techniques is that they are not site-specific and often require that the starting material be sectioned into smaller and smaller pieces, thereby destroying much of the original sample.

Other techniques generally referred to as "lift-out" techniques use focused ion beams to cut the sample from a substrate or bulk sample without destroying or damaging surrounding parts of the substrate. Such techniques are useful in analyzing the results of processes used in the fabrication of integrated circuits, as well as materials general to the physical or biological sciences. These techniques can be used to analyze samples in any orientation (e.g., either in cross-section or in plan view). Some techniques extract a sample sufficiently thin for use directly in a TEM; other techniques extract a "chunk" or large sample that requires additional thinning before observation. In addition, these "lift-out" specimens may also be directly analyzed by other analytical tools, other than TEM. Techniques where the sample is extracted from the substrate within the focused ion beam ("FIB") system vacuum chamber are commonly referred to as "in-situ" techniques; sample removal outside the vacuum chamber (as when the entire wafer is transferred to another tool for sample removal) are call "ex-situ" techniques.

Samples which are sufficiently thinned prior to extraction are often transferred to and mounted on a metallic grid covered with a thin electron transparent film for viewing. FIG. 1A shows a sample mounted onto a prior art TEM grid 10. A typical TEM grid 10 is made of copper, nickel, or gold. Although dimensions can vary, a typical grid might have, for example, a diameter of 3.05 mm and have a middle portion 12 consisting of cells 14 of size 90×90 $\mu m^2$ and bars 17 with a width of 35 μm. The electrons in an impinging electron beam will be able to pass through the cells 14, but will be blocked by the bars 17. The middle portion 12 is surrounded by an edge portion 16. The width of the edge portion is 0.225 mm. The edge portion 16 has no cells, with the exception of the orientation mark 18. The thickness 15 of the thin electron transparent support film is uniform across the entire sample carrier, with a value of approximately 20 nm. A thin carbon film 19 is attached to the bottom side of TEM grid 10. TEM specimens to be analyzed are placed or mounted within cells 14 on top of carbon film 19.

In one commonly used ex-situ sample preparation technique, a protective layer 22 of a material such as tungsten is deposited over the area of interest on a sample surface 21 as shown in FIG. 2 using electron beam or ion beam deposition. Next, as shown in FIGS. 3-4, a focused ion beam using a high beam current with a correspondingly large beam size is used to mill large amounts of material away from the front and back portion of the region of interest. The remaining material between the two milled rectangular trenches 24 and 25 form a thin vertical sample section 20 that includes an area of interest. The angle of the FIB (not shown) used in the milling is generally angled at 90° from the sample surface 21. This allows for the FIB to mill straight down. The trench 25 milled on the back side of the region of interest is smaller than the front trench 24. The smaller back trench is primarily to save time, but the smaller trench also prevents the finished sample from falling over flat into larger milled trenches which may make it difficult to remove the specimen during the micromanipulation operation. When sample section 20 is eventually extracted, it will lay horizontally on a TEM/STEM machine exposing a TEM normal viewing side 23.

As shown in FIG. 5, once the specimen reaches the desired thickness, the stage is tilted and a U-shaped cut 26 is made at an angle partially along the perimeter of the sample section 20, leaving the sample hanging by tabs 28 at either side at the top of the sample. The sample section 20 that is cut out has a TEM normal viewing side 23 in the shape of a rectangle. The small tabs 28 allow the least amount of material to be milled free after the sample is completely FIB polished, reducing the possibility of redeposition artifacts accumulating on the thin specimen. The sample section is then further thinned using progressively finer beam sizes. Finally, the tabs 28 are cut to completely free the thinned lamella 27. When the lamella 27 is cut out and placed horizontally—The lamella 27 is generally a rectangular shape. Once the final tabs of material are cut free lamella 27 may be observed to move or fall over slightly in the trench.

In ex-situ processes, the wafer containing lamella 27 is removed from the vacuum chamber containing the FIB and placed under an optical microscope equipped with a micromanipulator. A probe attached to the micromanipulator is positioned over the lamella and carefully lowered to contact it. Electrostatic forces will attract lamella 27 to the probe tip 28 (shown in FIG. 6) or the micromanipulator can have a hollow center wherein it can create a vacuum through the probe tip to secure the lamella. The tip 28 with attached lamella 27 is then typically moved to a TEM grid 10 as shown in FIG. 7 and lowered until lamella 27 is placed on the grid in one of the cells 14 between bars 17. FIG. 8 is a picture of a lamella 27 on a traditional carbon grid. As shown in FIG. 8, even with the successful transportation of lamella 27 onto the carbon film 19, the orientation of the lamella 27 is difficult to determine. On account of the general rectangular shape of the lamella, it is difficult to determine whether the lamella 27 has turned 180° or has been inverted during the process of moving the lamella 27 from the vacuum chamber to the carbon grid 13.

The use of traditional carbon grid 13 poses a technical problem. The carbon grid 13 includes a carbon film 19 that can impact chemical analysis, such as EDS or EELS. Electron energy loss spectroscopy (EELS) is a form of spectroscopy wherein a material is exposed to a beam of electrons with a known, narrow range of kinetic energies. By measuring the amount of energy loss, the spectroscopy can determine the types of atoms, and the numbers of atoms of each type in a given sample. EELS is a compliment to energy-dispersive x-ray spectroscopy (variously called EDX, EDS, XEDS, etc.), which is another common spectroscopy technique available on many electron microscopes. EDX has the capability to identify the atomic composition of a material that is sensitive to heavier elements. In order to reduce the impact of the carbon background in chemical analysis, various analytical techniques will subtract the background interference of the carbon film.

Another typical procedure for studying lamella uses in-situ analysis. A common in-situ extraction technique is described in U.S. Pat. No. 6,570,170 to Moore, which describes extracting out a sample by making a "U"-shaped cut and then cutting the sample at an angle from the missing side of the "U" to undercut and free the sample. After the sample is freed, a probe 42 is attached to the sample by FIB-induced chemical vapor deposition and it is lifted out. This process typically results in a chunk-type sample 30, which is generally wedge shaped and approximately 10×5×5 μm in size. This sequence of steps is illustrated in FIG. 9 and FIG. 10.

In-situ and ex-situ methods of TEM sample preparation have their own advantages, but they also have their own shortcomings. In in-situ methods, each of the lamella is cut, attached to the microprobe, and attached to the sample holder individually. The individual manipulation of the lamella provides a high degree of confidence in knowing the orientation of the lamella. But these methods are typically very time-consuming and labor intensive. It further requires the sample to be welded or affixed to a TEM grid inside a vacuum chamber, which requires a large amount of valuable FIB time. In addition, because the process is performed over carbon films, analytical techniques are required to subtract the carbon background information by sampling the carbon film areas outside the lamella. In addition, CD metrology often requires multiple samples from different locations on a wafer to sufficiently characterize and qualify a specific process. In some circumstances, for example, it will be desirable to analyze from 15 to 50 TEM samples from a given wafer. When so many samples must be extracted and measured using known methods, the total time to process the samples from one wafer can be days or even weeks. Even though the information that can be discovered by TEM analysis can be very valuable, the entire process of creating and measuring TEM samples has historically been so labor intensive and time consuming that it has not been practical to use this type of analysis for manufacturing process control.

Although ex-situ methods do not require the labor intensive and time consuming manipulation inside the vacuum chamber, they are unreliable and require a great deal of operator experience. Even with experienced operators, the success range is only about 90%. It can be time consuming and difficult to locate a lamella site and the extraction probe must be very carefully moved into position to avoid damaging the sample or the probe tip. Once a lamella has been completely freed, it can move in unpredictable ways; it can fall over in the trench or in some cases it can actually be pushed up and out of the trench by electrostatic forces. This movement can make it difficult to locate and/or pick up the lamella with the extraction probe. The electrostatic attraction between the probe and the sample is also somewhat unpredictable. In some cases, the lamella may not stay on the probe tip. Instead, it can jump to a different part of the probe. In other cases, the lamella may fall off while the sample is being moved. If the lamella is successfully transferred to the TEM grid, it can be difficult to get the lamella to adhere to the grid support film rather than the probe tip. The lamella will often cling to the probe tip and must be essentially wiped off onto the film. As a result, it is difficult to control the precise placement or orientation of the lamella when it is transferred to the TEM grid. The lamella typically has a region of interest that is intended for imaging. If the lamella 27 is close to bars 17, it is often difficult to determine if the region of interest is properly placed over the carbon grid and if the region of interest is properly aligned with the holes in the carbon film.

Some carbon films that are used with TEM lamella analysis are carbon grids with holes. Carbon grids with holes, such as the Quantifoil™ 2:1 grids provide the ability to position a region of interest over the holes such that there is less optical and spectral interference with the carbon. A typical carbon grid of this characteristics will have a hole size of 2 µm. Unfortunately, the region of interest in the lamella often exceed 2 µm in length, and the typical carbon grids with holes are not able to fully contain the region of interest. Even with superior TEM systems, the optical chain and mechanical motion control has at least 1 µm of error during placement. This results in a failure to properly place the region of interest in nearly 80% of the cases.

Experienced ex-situ plucking users can use a standard glass rod micro manipulator to move and orient the lamella 27 based on optical imaging systems, but any unforeseen motion on the lamella 27 during the plucking and placing process eliminates any confidence of orientation. Unforeseen motion during the process occurs approximate 25% of the time. In addition, the ability to set the sample into a very specific region of interest has a large amount of uncertainty.

What is needed is an improved method for TEM sample analysis, including an ability to create samples that allow for easy orientation of the lamella so that its region of interest can be properly imaged with little to no interference from the carbon film during chemical analysis.

SUMMARY OF THE INVENTION

An object of the invention, therefore, is to provide an improved method for TEM sample analysis. Preferred embodiments of the present invention provide for improved methods for creating and using a lamella with easily identifiable orientation. Some preferred embodiments of the present invention provide the use of the lamella in an ex-situ process that allows for lamella sample placement on a carbon grid with a high degree of confidence regarding its orientation and overall faster processing of the lamella than current prior art in-situ processes.

Some preferred embodiments of the present invention provide methods to create lamella having an asymmetric shape, which allows for higher degree of orientation recognition and easier identification of the region of interest on the lamella. Some preferred embodiments of the present invention provide methods to properly place the lamella over a carbon grid containing holes such that the region of interest lies directly over one of the holes such that TEM imaging and chemical analysis of the sample results in little to no interference from the carbon.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIGS. 2-5 illustrate prior art steps in an ex-situ sample preparation technique;

FIG. 8 is a close-up picture of the carbon grid including lamellas on the carbon film;

FIGS. 9-10 illustrate prior art in-situ removal of a sample that is intended for attachment;

DETAILED DESCRIPTION OF PREFERRED EMBODIMENTS

Preferred embodiments of the present invention provide for improved methods for lamella creation from wafers and use of the lamella in ex-situ processes. More specifically, preferred embodiments make lamellas in asymmetric shapes before they are extracted and placed on specified carbon grids containing a carbon film with sizeable holes. S/TEM samples produced according to the present invention will allow S/TEM imaging and chemical analysis with a high degree of confidence in sample orientation. Such orientation and methods of using ex-situ processes allow for proper placement of the sample on precise locations of the carbon grid such that the region of interest lies over one of the many sizable holes in the carbon film, which results in little to no optical and spectral interference from the carbon. Overall, the lower potential for error from knowing the orientation of the sample in combination with the faster processing of the samples in ex-situ processes and less interference from the carbon film results in increased throughput and reduction of cost of TEM lamella creation.

Figure 7:
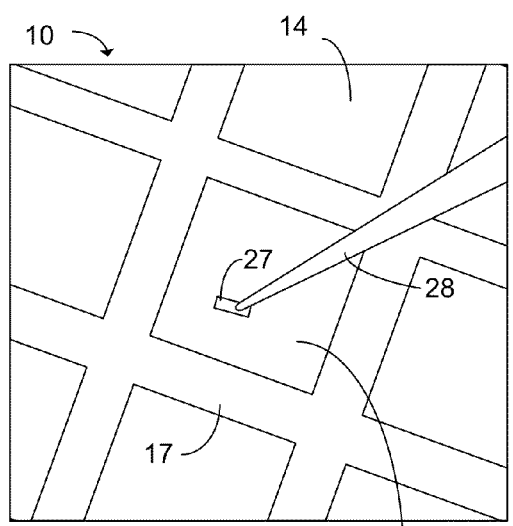

Although one of the preferred embodiments of the present invention uses carbon film containing 5×5 μm holes, other types of carbon grids are suitable, including 3 mm TEM grids manufactured by FEI, such as the "Multi" or "Auto Loader" grids containing similar sizable holes. Traditional carbon grids do not have sizable holes. A typical region of interest in a lamella is at least 2 μm in length. Carbon grids having holes with 2 μm dimensions or less are not capable of containing the entirety of the region of interest. The proper placement of the sample over one of the sizeable holes in accordance with preferred embodiments of the present invention would place the region of interest of the lamella over one of the holes, which would reduce the spectral and optical interference created by the carbon film. In accordance with FIG. 7, a glass rod 28, or some other form of mechanical manipulator, places lamella 27 in between cells 14 and on top of the carbon film 19. Under the traditional methods of TEM analysis, a broad beam of electrons is projected and passes through lamella 27 and passes through carbon film 19. The electrons that are transmitted through the lamella 27 and the carbon film 19 and are then focused to form an image of the sample. Carbon film 19 creates unwanted spectral and optical interference for chemical analysis, so typically, the interference caused by the carbon film 19 is measured by taking a TEM measurement of nearby carbon film 19 without the lamella 27 and subtracting the interference from the final image.

Figure 11A:
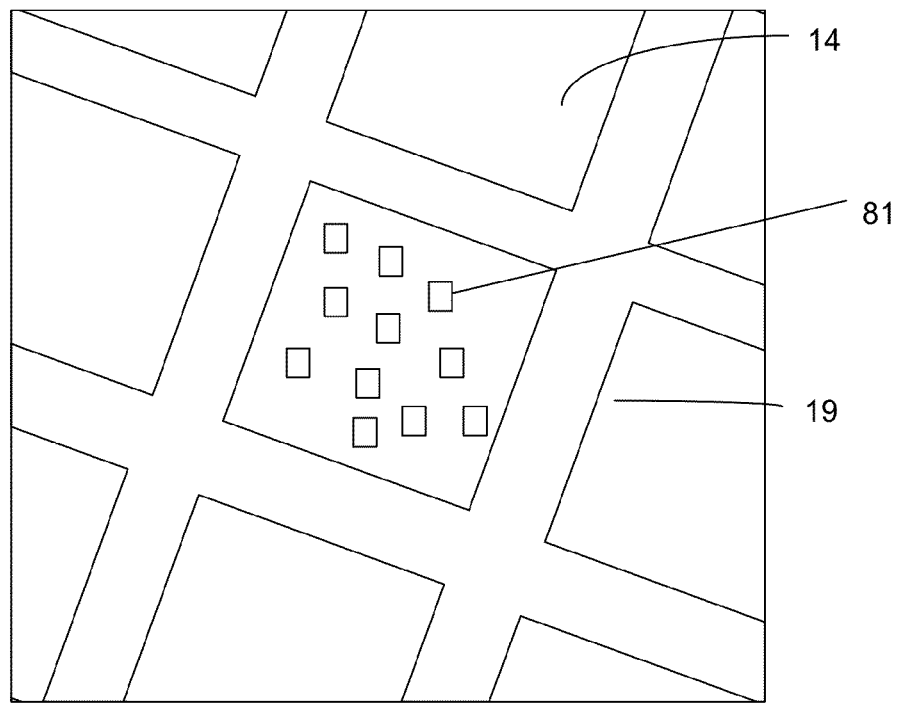
FIG. 11A shows a carbon grid in accordance with preferred embodiments of the invention having 5×5 µm holes (not drawn to scale)
Figure 11B:
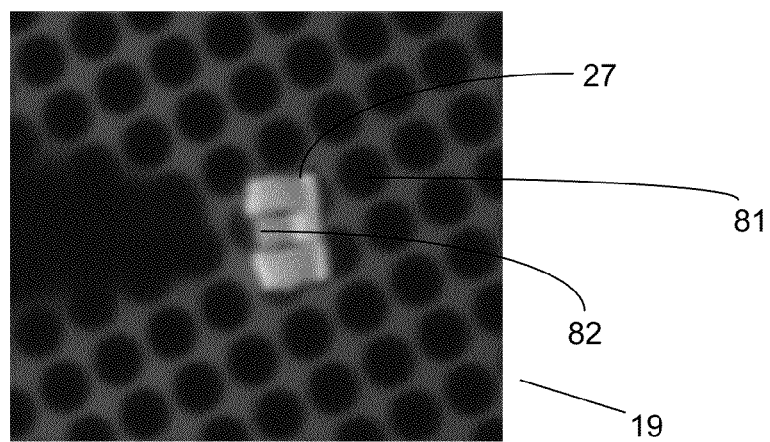
FIG. 11B shows a picture of a lamella lying over a carbon grid wherein the region of interest lies over a hole.

One of the problems associated with subtracting the interference of the carbon film 19 is the level of inconsistency in carbon film 19. Various areas of carbon film 19 have varying thicknesses and imperfections. The TEM reading of nearby carbon film 19 may not be an exact match of the carbon film behind lamella 27 during imaging, which would result in inaccurate subtraction of interference measurements. Thus, the preferred embodiments of the present invention allows for the attachment of lamella 27 to the carbon grid 13 such that the entirety of the region of interest lies over one of the sizeable holes, such as 5×5 μm holes. FIG. 11A shows a carbon grid in accordance with the embodiments of the present invention. Carbon grid 13 contains 5×5 μm holes 81. Holes 81 are randomly placed and are not to scale. FIG. 11B is an actual picture showing the placement of a lamella 27 on a carbon film 19 with the region of interest 82 placed directly over a sizeable hole 81 in accordance with the embodiments of the present invention.

Figure 12:
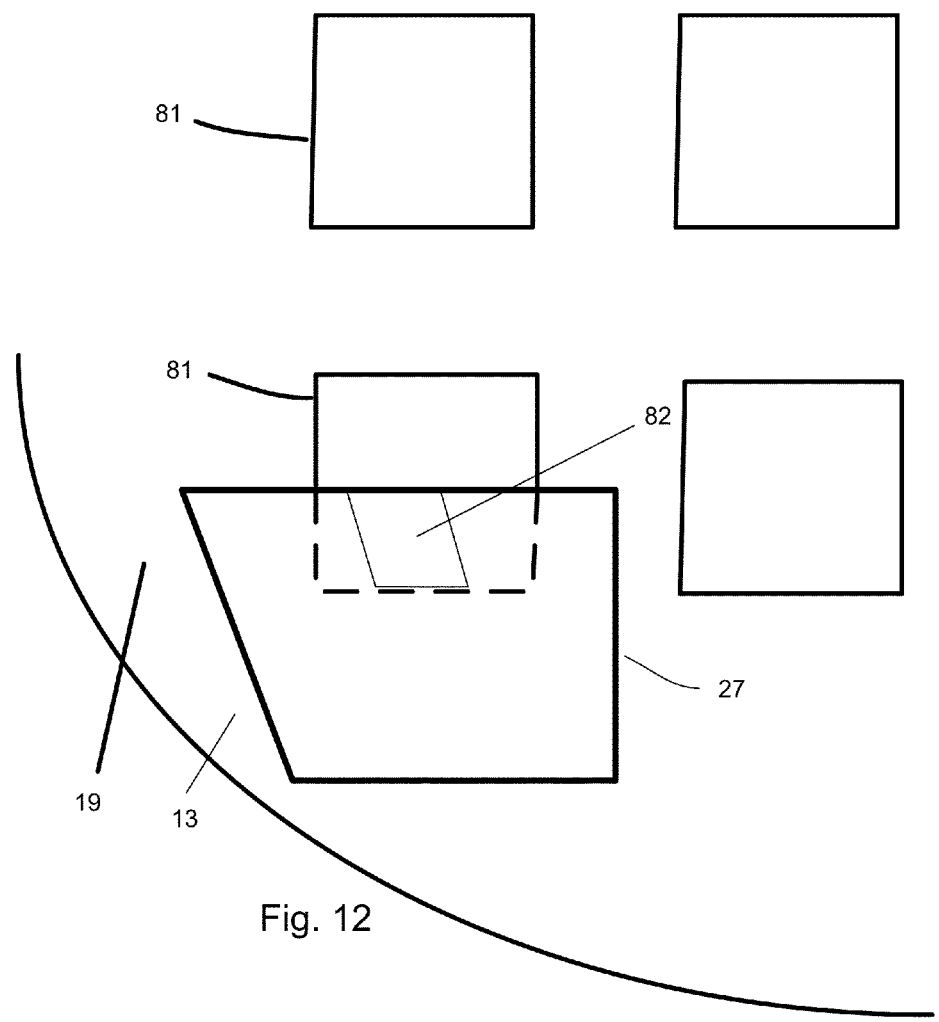
FIG. 12 shows a schematic in accordance with preferred embodiments of the invention showing a lamella over a hole on the carbon grid.

FIG. 12 shows a schematic of the lamella placement on carbon grid 13 in accordance with preferred embodiments of the invention. Lamella 27 has a region of interest 82. The proper placement of lamella 27 results in no carbon film being behind the region of interest 82. The absence of the carbon film behind the region of interest 82 results in little to no optical and spectral interference from TEM processing and chemical analysis.

Figure 13:
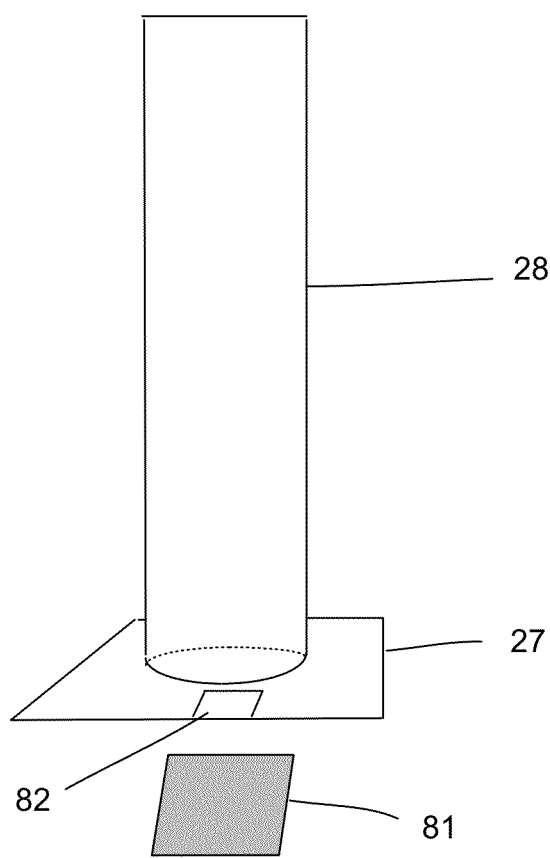
FIG. 13 shows the placement of lamella using a microprobe glass rod.

FIG. 13 shows a schematic of placing lamella 27 over hole 81. Using a sample holder, such as a glass rod 28 or some other mechanical manipulator, lamella 27 is carefully placed over hole 81 such that the region of interest 82 lies over hole 81. The size of the region of interest 82 is between 2 and 5 μm in length. The level precision required for the proper aligning of the region of interest 82 for this method is high and results in placement errors of 1 μm in some cases. Due to the uncertainty created by the static electric forces, knowing the proper orientation of lamella 27 and the exact location of the region of interest 82 would reduce the error in proper placement.

Figure 1:
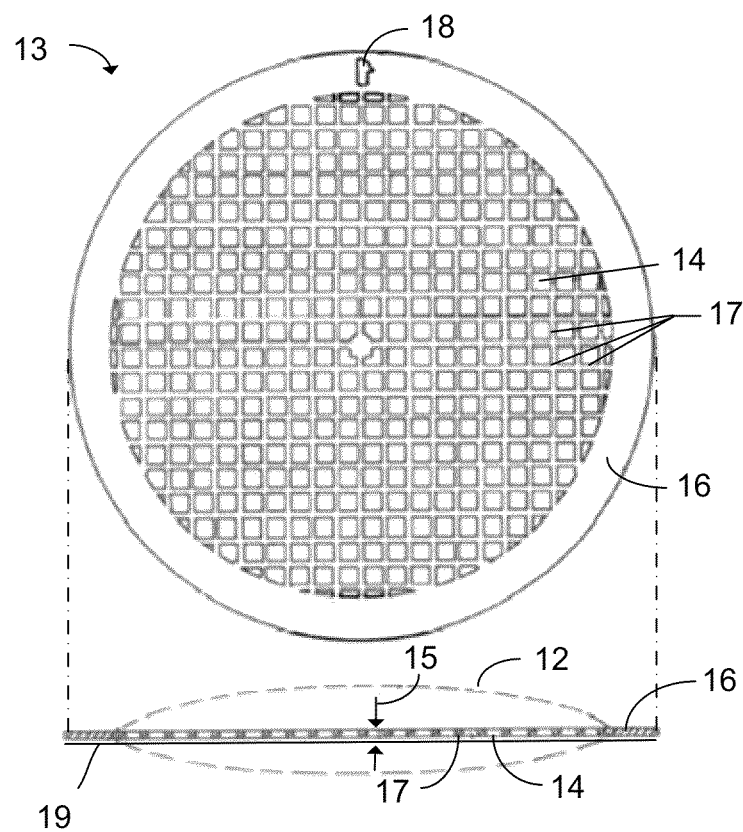
FIG. 1 shows a typical TEM grid.
Figure 5:
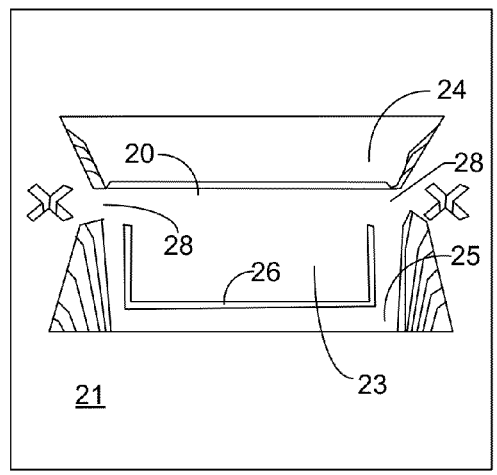
Figure 6:
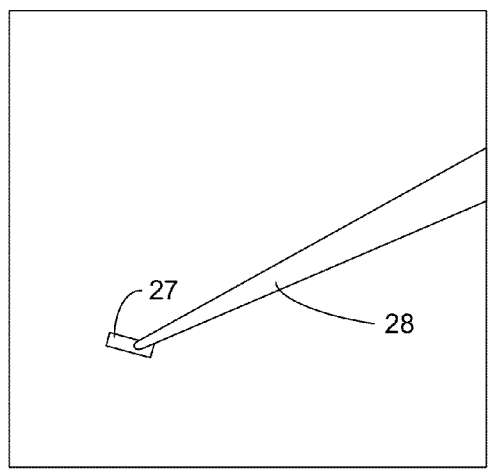
FIGS. 6-7 illustrate the transfer of a lamella using a probe and electrostatic attraction according to the prior art.

Typical lamellas have symmetrical shapes, such as rectangles and squares. The FIB and electron beam milling and processing is typically performed at a 90° angle from the surface of the wafer and its sample surface 21. The rectangular or square shape is generally the easiest shape to manufacturing requiring the least amount of FIB or electron beam milling during the lamella creation. FIG. 5 shows a schematic of large milled trenches 24 and 25 that are produced from a focused ion beam using a high beam current that is angled at 90° from the sample surface 21. The orthogonal beam current creates a remaining lamella 20 with a TEM-normal viewing side 23 that is rectangular. Once the sample stage holding he sample is rotated, the FIB is used to cut U-shaped incision 26 creating the symmetric rectangular lamella. Typically, the TEM-normal viewing side 23 of the lamella 27 usually has a ratio of width to height that is near to 1, ranging generally from 1.0 to 2.0.

The limited aspect ratio and the symmetrical shape of the lamella 27 provide very little visual indication of its orientation when lamella 27 is placed on carbon grid 13. Although the electrostatic forces that attaches glass rod 28 with lamella 27 are strong, the random forces can inadvertently invert the lamella 27 or turn it 180° resulting in improper identification of the region of interest 82. The overall small size in conjunction with the limited aspect ratio makes placement of lamella 27 over the hole 81 a difficult procedure.

Figure 14:
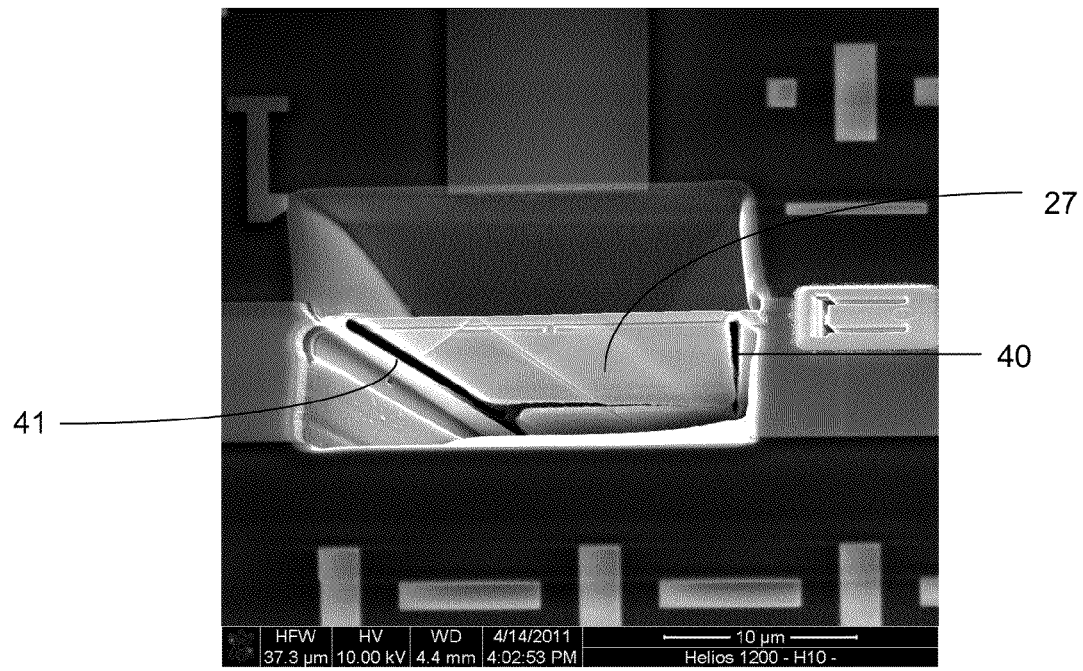
FIG. 14 shows a picture of the formation of an asymmetric lamella in accordance with preferred embodiments of the invention.
Figure 15:
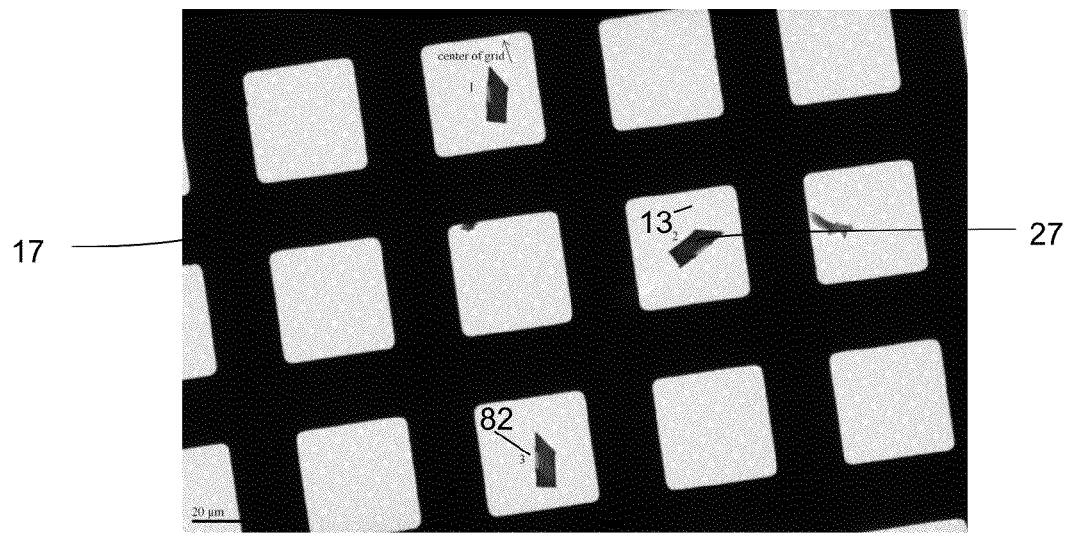
FIG. 15 shows a picture of the asymmetric lamellas lying on a carbon grid.

In accordance with the present embodiments of the invention, a method of manufacturing an asymmetric lamella is disclosed. An asymmetric lamella wherein the orientation of lamella 27 is apparent solves the confusion regarding the location and identification of the region of interest 82. FIG. 14 shows a picture of from the manufacturing process of an asymmetric lamella in accordance with some embodiments of the present invention. The shape of the asymmetric lamella 27 is a convex quadrilateral with one straight side 40 and one obtuse side 41. More specifically, the convex quadrilateral is a right trapezoid having two parallel sides. FIG. 15 is a picture of a carbon grid 13 and a number of lamellas lying on the grid. When an asymmetric lamella 27 is placed on carbon grid 13, the orientation of lamella 27 and the location of the region of interest 82 are unmistakable. The user is able to quickly identify the location of the region of interest 82, which results in higher efficiency when placing lamella 27 over hole 81 on carbon film 19.

Figure 16:
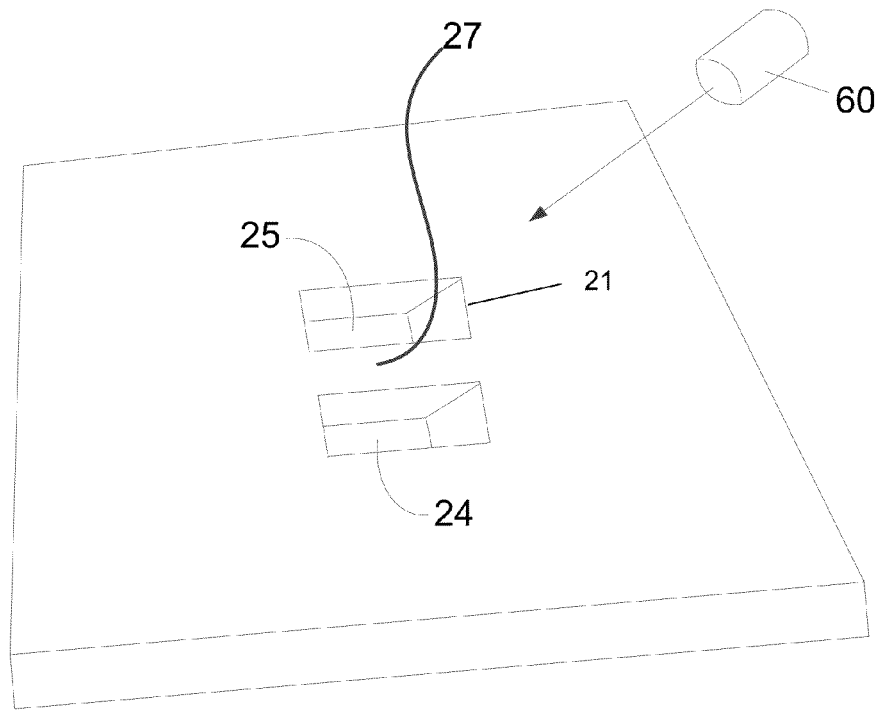
FIG. 16 shows a graphical representation of an FIB system making a lamella in accordance with the preferred embodiments.
Figure 17:
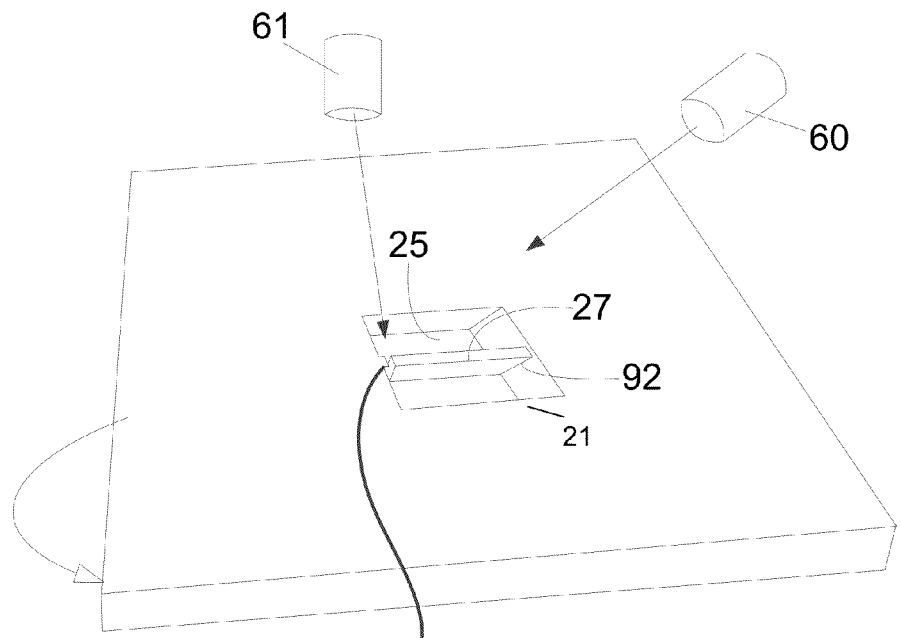
FIG. 17 shows a graphical representation of an FIB system making incisions to cut out an asymmetric lamella in accordance with the preferred embodiments.

Traditional milling of the lamella involves orienting the sample surface 21 from the FIB 60 and milling trenches 24 and 25 that are substantially at an orthogonal angle to the sample surface 21. Traditional milling angles provide box shaped trenches and results in a lamella having a TEM normal view that is rectangular. FIGS. 16 and 17 show the schematics involved with manufacturing the asymmetric lamella 27 in accordance with the preferred embodiments of the present invention. The sample stage is capable of rotating on an X-Y plane as shown in FIG. 17. In some embodiments of the present invention, the sample surface 21 is at 45° angle with the FIB 60. It is not required that the FIB 60 be at an exact 45° angle. Other oblique angles are considered and able to perform the necessary milling. The milling of the side trenches 24 and 25 is performed at a 45° angle. In accordance, trenches 24 and 25 are milled such that the sideview of the trenches are in the shape of a parallelogram. Once trenches 24 and 25 are milled, the sample stage is turned on the X-Y direction so that the FIB 60 is pointing towards one of the sides of the lamella 27. The FIB 60 makes two separate incisions. The first incision 92 is at the same 45° angle as the milled trenches. The second incision 93 is angled orthogonally with the sample surface 21. The resultant shape of lamella 27 is a right trapezoid, which is an asymmetric shape in accordance with embodiments of the present invention.

Figure 18:
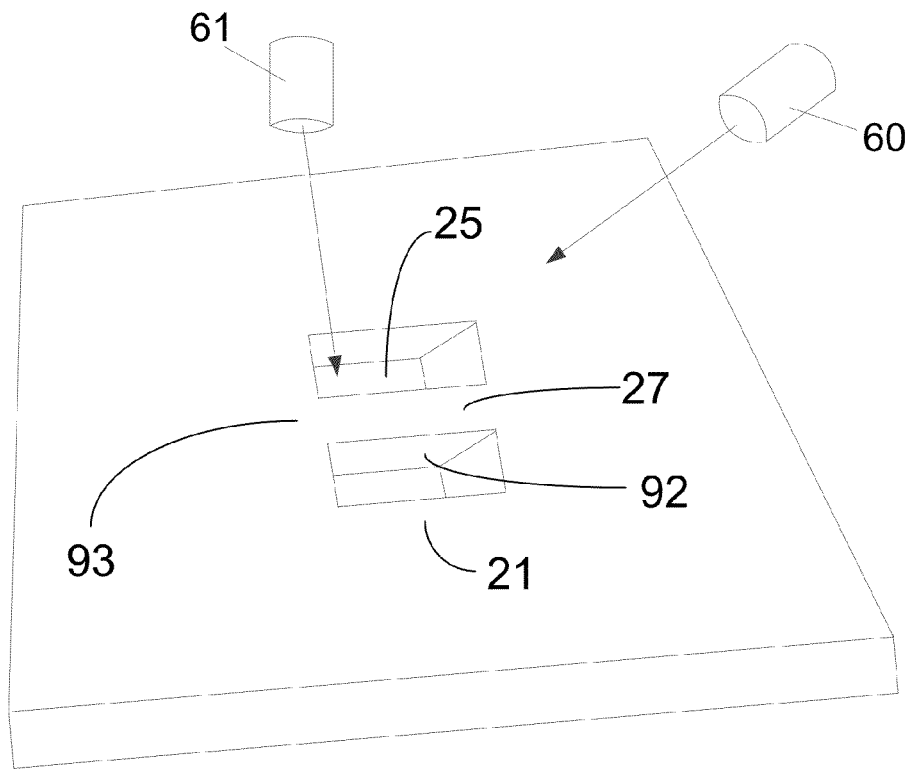
FIG. 18 shows a graphical representation of an FIB system having two FIBs in accordance with another embodiment of the present invention.
Figure 19:
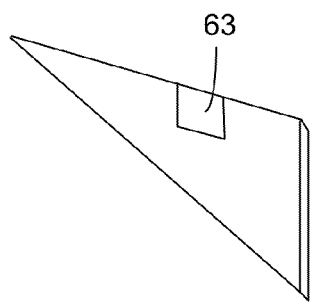
FIG. 19 shows a triangular asymmetric lamella.

As shown in FIG. 18, in accordance with another embodiment of the present invention, it is possible to have an additional FIB 61 that is angled orthogonally with sample surface 21. In this embodiment, both FIB 60 and FIB 61 are used to create incisions 92 and 93 on lamella 27 without the need to rotate the sample stage in the XY direction. It is also contemplated that various angles other than 45° angles be used in placing the additional FIB. Various oblique angles can be used to create one side that is different than the other. The flexibility of the XY rotation of the sample stage in combination with the versatility of the FIB or FIBs location (and/or the use of a dual beam or laser beam) allows for the creation of other asymmetric lamellas. As shown in FIG. 19, an asymmetric triangle can also provide a degree of orientation and proper identification of the region of interest 63. As long as the lamella has a cross-section area that is large enough to allow ex-situ processing and a finite sized plucking contact area, lamellas having five or more sides are also included in the embodiments of the present invention (not shown). All other edges should be chosen with dimensions to minimize the FIB volume removed while simultaneously satisfying the requirements for asymmetric formation. It should be noted that there are associated challenges in creating other asymmetric shapes on account of the fragility of the lamella and various angles needed for the FIB milling.

Figure 20:
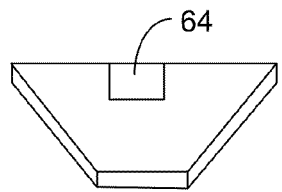
FIG. 20 shows a lamella have top to bottom asymmetry.

For purposes of the present invention, the term asymmetry is defined as lacking correspondence on either side of a dividing line, plane, center, or axis. Overall, the higher degree of orientation of lamella 27 using an asymmetric shape allows for the proper identification of the region of interest. Although a lamella having complete asymmetry allows for the highest degree of orientation recognition, it is possible to have top to bottom bilateral asymmetry. FIG. 20 shows yet a further embodiment of the current invention. Although the left and right side are symmetrical, the top to bottom asymmetry provides a level of orientation that is improved from traditional rectangular lamellas. The region of interest 64 in this bilateral asymmetric lamella would also be easier to identify even under low resolution magnification.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for ex-situ TEM/STEM/SEM analysis comprising:
   creating multiple samples within a vacuum chamber with a focused ion beam, wherein said samples have an asymmetric TEM-normal viewing side;
   each sample having a region of interest for TEM/STEM/SEM analysis;
   removing samples from the vacuum chamber and placing them on a carbon grid containing a carbon film wherein the carbon film has multiple about 2 μm holes;
   said samples being placed on the carbon grid wherein the asymmetric TEM-normal viewing side of each sample allows for the proper orientation of each region of interest in said samples to lie substantially over one of said holes; and wherein multiple samples contain an asymmetric shape that allows for the proper placement of each region of interest over the holes; and wherein the analysis of the samples provides an analysis of the region of interest without any carbon background interference.

2. The method of claim 1 further comprising the processing of said sample with a TEM or SEM or STEM with a source of electrons wherein there is little to no optical or spectral interference from said carbon film.

3. The method of claim 2 wherein said processing of said sample with a TEM or SEM or STEM includes a chemical analysis employing an EDS or EELS.

4. The method of claim 1 wherein said asymmetric shape is a right trapezoid.

5. The method of claim 1 wherein the region of interest of each sample is at least 2 μm in length.

6. The method of claim 1 wherein the removal of said sample from said vacuum chamber and placement of said sample on said carbon grid is done with a glass rod.

7. The method of claim 1 wherein the creation of the asymmetric sample is done by a dual focused beam system including a focused ion beam and an electron beam.

* * * * *